United States Patent [19]

Magnusson et al.

[11] Patent Number: 5,370,221
[45] Date of Patent: Dec. 6, 1994

[54] FLEXIBLE PACKAGE FOR BONE CEMENT COMPONENTS

[75] Inventors: Bent Magnusson, Birkerod, Denmark; Daniel B. Smith, Warsaw; Ronald L. Gilbert, Fort Wayne, both of Ind.

[73] Assignees: Biomet, Inc., Warsaw, Ind.; Polymers Reconstructive A/S, Farum, Denmark

[21] Appl. No.: 113,414

[22] Filed: Aug. 27, 1993

Related U.S. Application Data

[63] Continuation-in-part of Ser. No. 11,339, Jan. 29, 1993.
[51] Int. Cl.⁵ ............................................. B65D 81/32
[52] U.S. Cl. ................................. 206/221; 206/219; 206/524.8; 604/410; 604/416
[58] Field of Search ............ 206/219, 221, 438, 524.1, 206/568; 215/DIG. 8; 604/410, 416

[56] References Cited

U.S. PATENT DOCUMENTS

| | | |
|---|---|---|
| 2,605,896 | 8/1952 | Rohdin . |
| 2,690,179 | 9/1954 | Fox . |
| 2,756,875 | 7/1956 | Yochim . |
| 2,874,830 | 2/1959 | Birmingham . |
| 2,893,547 | 7/1959 | Earl et al. . |
| 2,932,385 | 4/1960 | Bollmeier et al. . |
| 2,971,851 | 2/1961 | Kurtz . |
| 3,028,000 | 4/1962 | Clements et al. . |
| 3,082,867 | 3/1963 | Gelpey . |
| 3,156,352 | 11/1964 | Hayhurst . |
| 3,294,227 | 12/1966 | Schneider et al. . |
| 3,462,070 | 8/1969 | Corella . |
| 3,608,709 | 9/1971 | Pike . |
| 3,809,224 | 5/1974 | Greenwood . |
| 3,847,279 | 11/1974 | Montgomery . |
| 3,964,604 | 6/1976 | Prenntzell . |
| 3,983,994 | 10/1976 | Wyslotsky . |
| 4,000,996 | 1/1977 | Jordan . |
| 4,023,675 | 5/1977 | Claasen . |
| 4,039,076 | 8/1977 | Desaules . |
| 4,211,019 | 7/1980 | McCafferty ........................ 206/219 |
| 4,277,184 | 7/1981 | Solomon . |
| 4,401,214 | 8/1983 | Kleckers ........................... 206/219 |
| 4,402,402 | 9/1983 | Pike . |
| 4,458,811 | 7/1984 | Wilkinson . |
| 4,462,224 | 7/1984 | Dunshee et al. . |
| 4,463,875 | 8/1984 | Tepic ................................. 206/219 |
| 4,608,043 | 8/1986 | Larkin . |
| 4,664,257 | 5/1987 | Nilson . |
| 4,721,390 | 1/1988 | Lidgren . |
| 4,795,265 | 1/1989 | Dahlberg et al. . |
| 4,798,288 | 1/1989 | Holzner . |
| 4,808,184 | 2/1989 | Tepic ........................... 215/DIG. 8 |
| 4,910,259 | 3/1990 | Kindt-Larsen et al. . |
| 4,927,012 | 5/1990 | Rowe . |
| 4,952,068 | 8/1990 | Flint . |
| 4,961,495 | 10/1990 | Yoshida et al. . |
| 4,973,168 | 11/1990 | Chan ................................. 206/219 |
| 4,994,056 | 2/1991 | Ikeda . |
| 5,051,482 | 9/1991 | Tepic ................................. 604/416 |
| 5,069,773 | 12/1991 | Frangioni . |
| 5,114,240 | 5/1992 | Kindt-Larsen et al. . |
| 5,121,302 | 6/1992 | Bay et al. . |

FOREIGN PATENT DOCUMENTS

| | | |
|---|---|---|
| 1054170 | 2/1954 | France . |
| 1258379 | 3/1961 | France . |
| WO84/03830 | 4/1984 | Japan . |
| 697723 | 9/1953 | United Kingdom . |
| WO8606618 | 11/1986 | WIPO . |
| WO90/13355 | 11/1990 | WIPO . |

Primary Examiner—Jimmy G. Foster
Attorney, Agent, or Firm—Harness, Dickey & Pierce

[57] ABSTRACT

A flexible container for packaging liquid and powder components that are to be mixed within the container to form a bone cement comprises a divider for dividing the container into first and second compartments and for isolating the components from one another, the first compartment containing the liquid component and the second compartment containing the powder component under vacuum, and a vacuum reservoir in communication with the second compartment, the vacuum reservoir being of sufficient size to receive substantially all residual interstitial gases from the powder component and thereby ensure thorough admixing of the liquid and powder components upon release of the divider. In an exemplary embodiment, the reservoir comprises an elongated cylinder which is either hollow and closed at least at one end by a respective filter element or formed of an open-cell foam, the interior of the hollow cylinder or the open-cell foam being of sufficient free volume to receive and hold under reduced pressure the interstitial air.

10 Claims, 10 Drawing Sheets

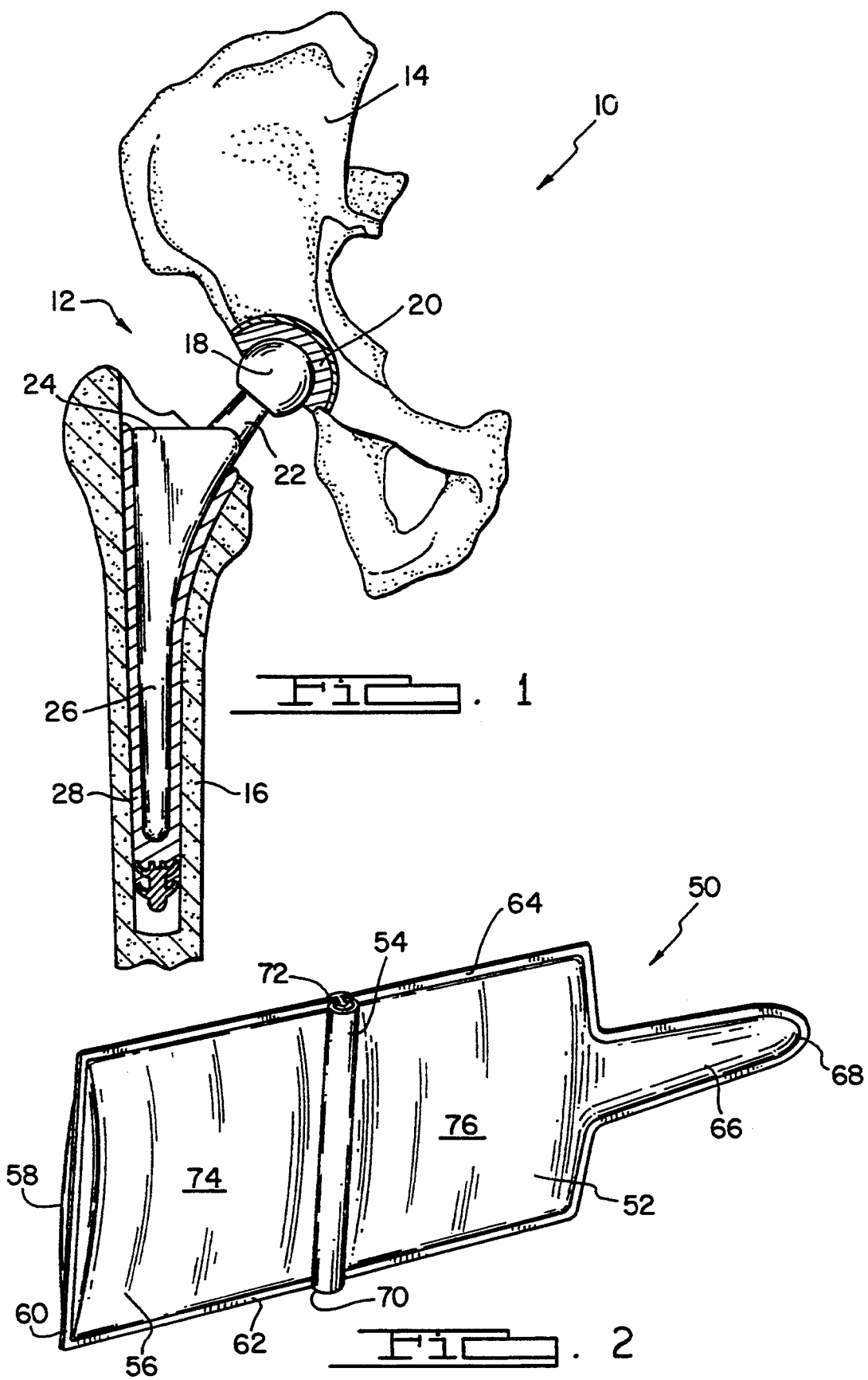

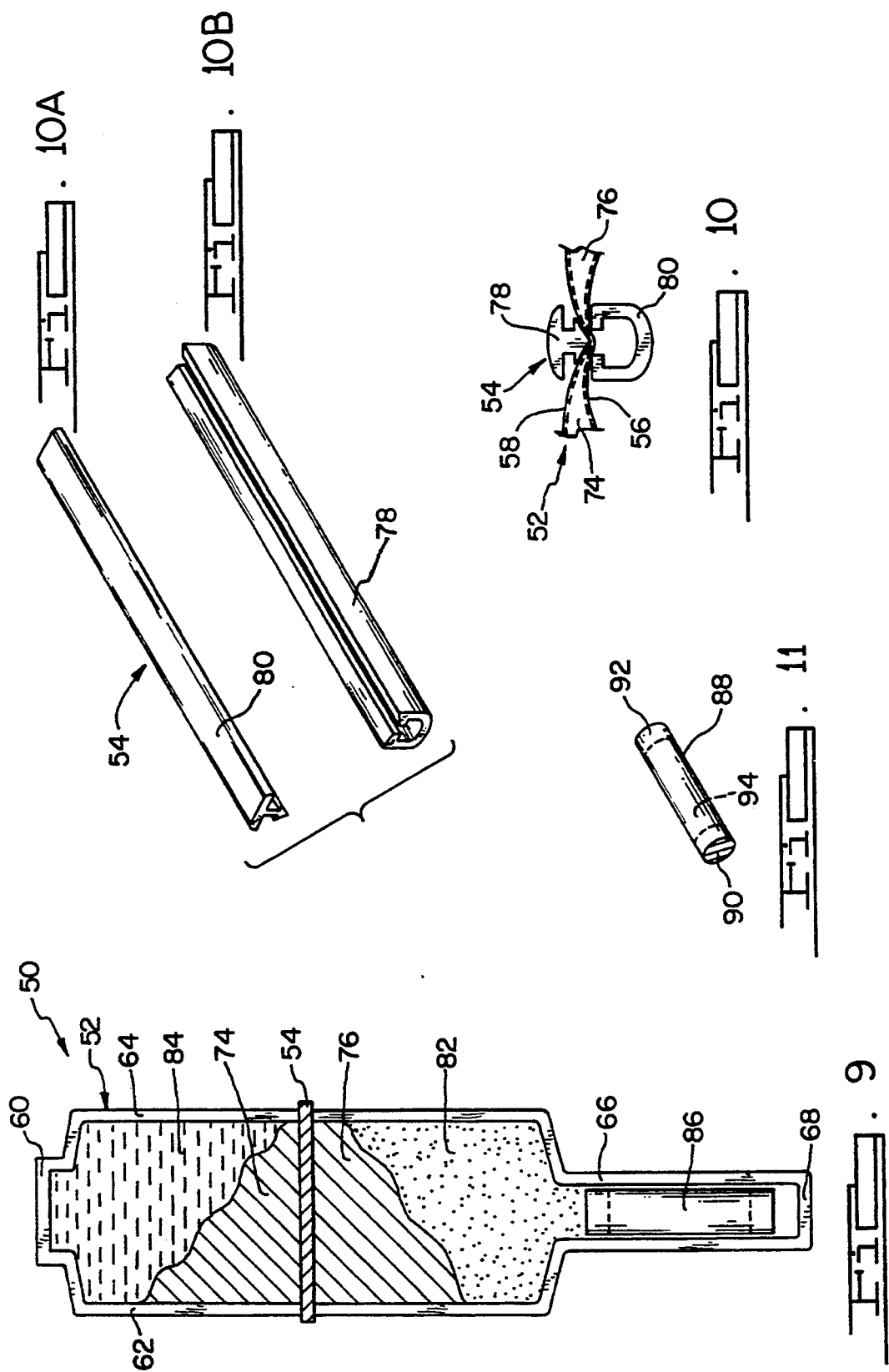

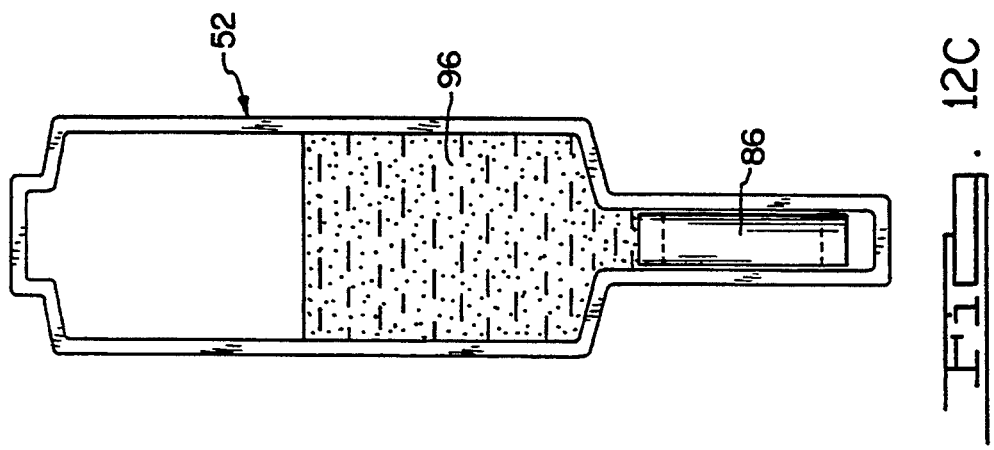
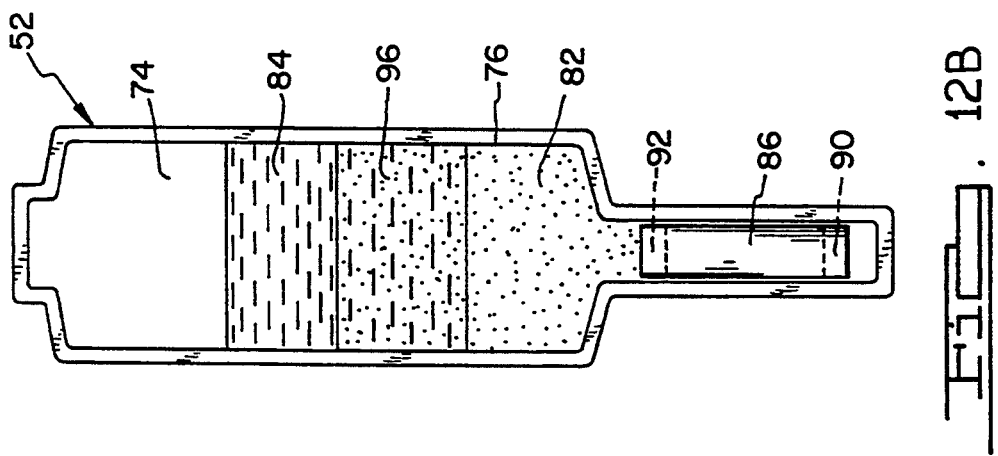
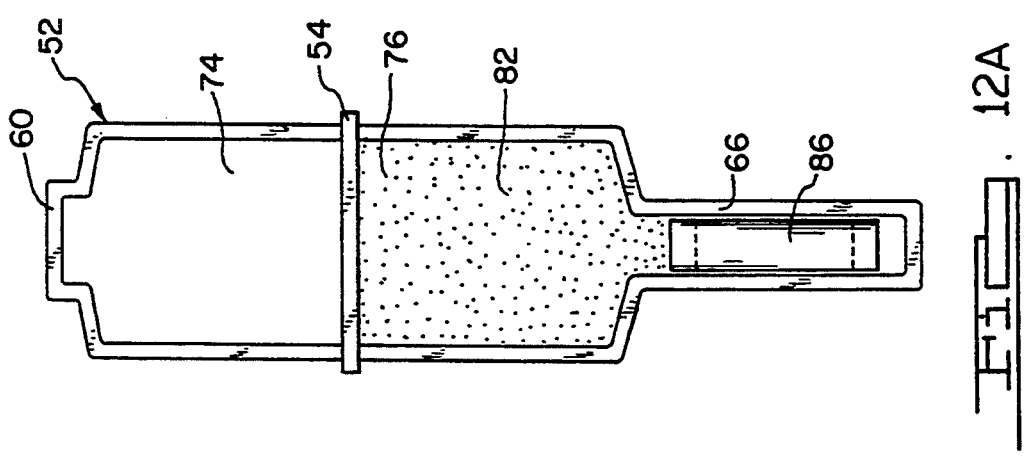

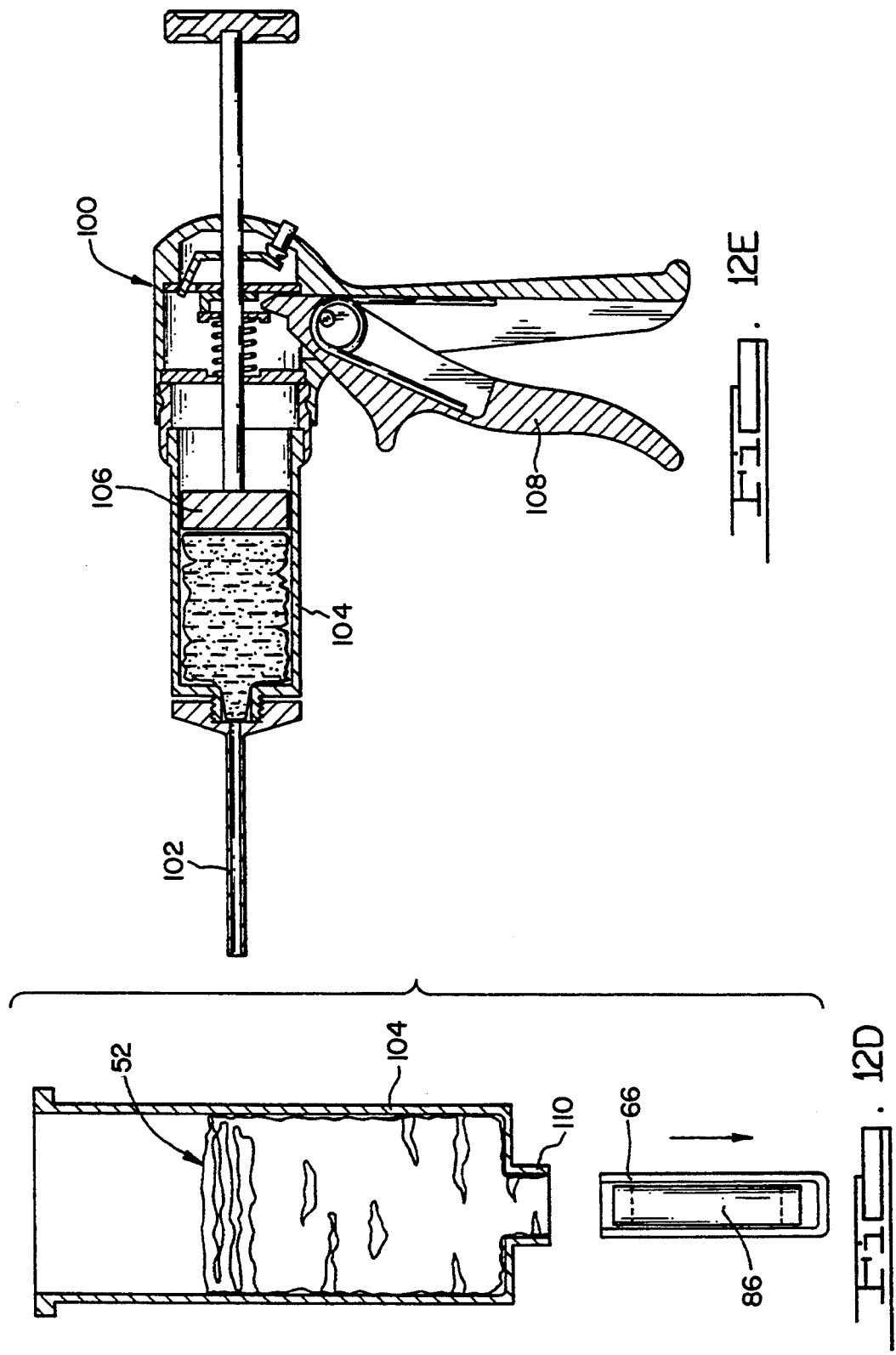

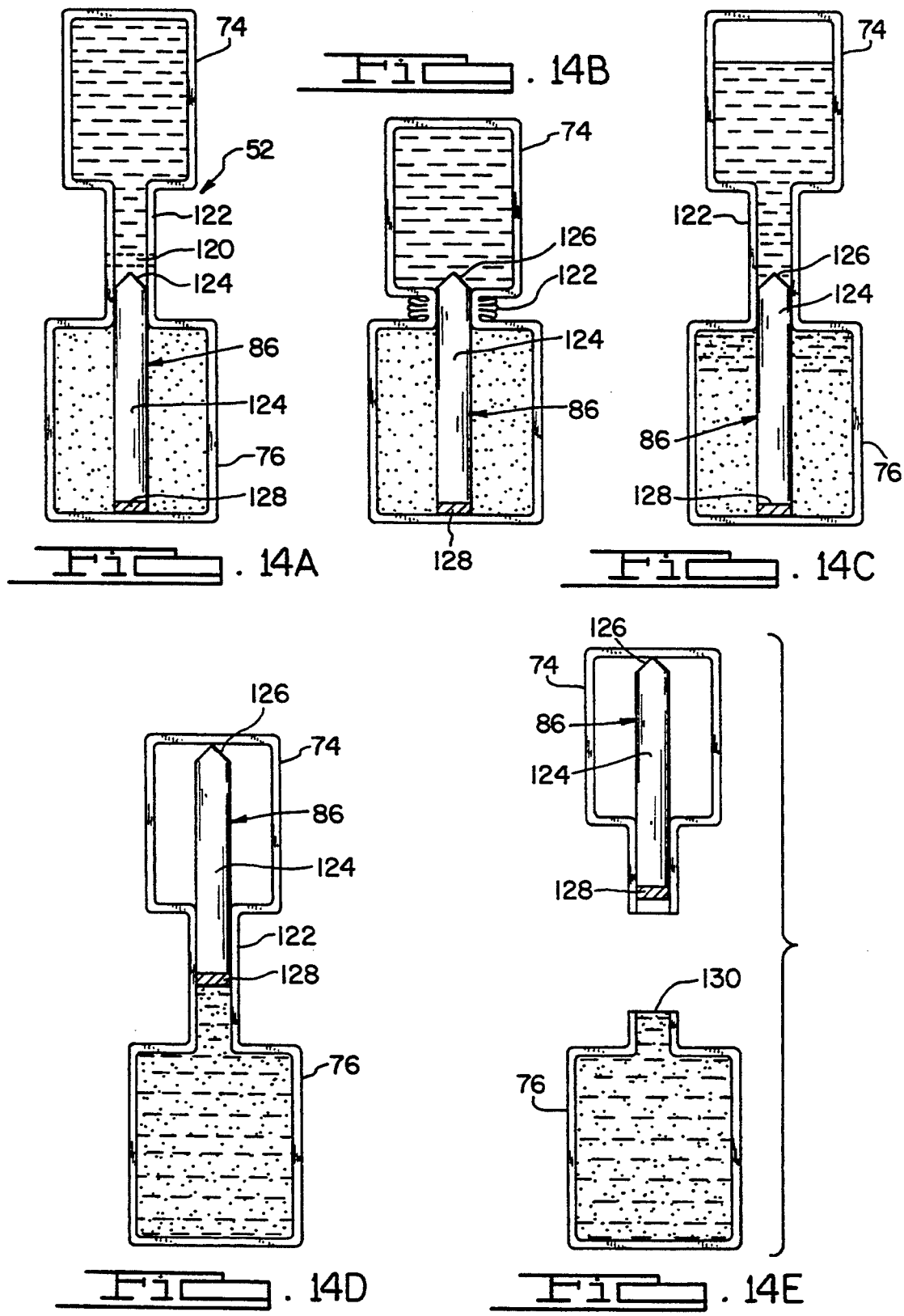

FLEXIBLE PACKAGE FOR BONE CEMENT COMPONENTS

This application is a continuation-in-part application of Ser. No. 08/011,339 filed Jan. 29, 1993.

BACKGROUND OF THE INVENTION

The present invention pertains to an apparatus and a method for packaging, mixing and delivering bone cement. More particularly, the present invention relates to apparatus for intimately mixing at least two components of bone cement wherein the components are initially kept in separate compartments of a flexible package.

The natural joints of the human body often undergo degenerative changes due to various etiologies. When these degenerative changes are advanced, irreversible and unresponsive to non-operative management, it may ultimately become necessary to replace the natural joint with a prosthetic device. When such replacement becomes necessary, the prosthetic device which is implanted is often secured to the natural bone by using bone cement.

Bone cement that is used to secure prosthetic devices to bone is comprised of a liquid monomer component that polymerizes about a polymeric powder component. In this regard, bone cement is generally formed from a methyl methacrylate monomer and poly (methyl methacrylate) or methyl methacrylatestyrene homo- or copolymer. The polymeric powder component of bone cement usually comprises particles composed of spherical beads that may be obtained by a suspension polymerization process. The beads are generally sieved to comply with particular size specifications. The powder component may also comprise particles that have been milled or crushed.

The preparation of bone cement generally involves mixing the polymer and monomer components in a suitable reaction vessel to form the bone cement. Generally, it is necessary that the components of bone cement be uniformly and thoroughly mixed so that a homogenous product is obtained. Increased homogeneity of the blend and minimal porosity are particularly desirable in providing a cement mixture that is easy to work with, yet maintains satisfactory mechanical properties. In producing bone cement it is crucial to maintain the liquid and the powder components separate until just prior to use and to avoid exposure of the components to the atmosphere because of the potentially malodorous nature of volatilized components of the bone cement.

There have been several approaches heretofore pertaining to the packaging and admixing in situ of a plurality of reactive components, also for cement products wherein the temporarily separated particulate solid component and liquid component are first combined, and then admixed in the packaging, without exposure to the atmosphere just prior to use. Representative approaches are disclosed in U.S. Pat. Nos. 2,874,830; 3,082,867; 4,041,214; 4,973,168; 4,463,875; and 5,114,240; and in PCT WO 86/06618.

The packaging systems proposed heretofore for use in the manufacture of bone cement products have often been found to have serious disadvantages when tested for commercialization. Quite often the packaging is overly complicated and expensive.

Some suggestions include the incorporation of diverse mechanical mixing devices into the packages in effort to attain the desired homogeneity and reduced porosity. Such devices are not only cumbersome, but the results obtained from using such devices are dependent on the skill and care of the individual performing the mixing operation. In this regard, the quality of the resulting bone cement in terms of porosity and homogeneity depends on the accuracy of transfer of the components, the mixing time, the mixing pattern and mixing speed, and if vacuum is used, on the time and pressure as well as the degree of mixing occurring under vacuum. All of the aforementioned parameters are determined by the individual operator and, as a result thereof, the homogeneity and the extent of polymerization (i.e., rheology of the cement during application) are neither consistent nor readily reproducible.

Accordingly, a need exists for a simple and inexpensive bone cement packaging system which will allow mixing of two or more components while avoiding the above-mentioned disadvantages.

SUMMARY OF THE INVENTION

The present invention provides a flexible packaging system for bone cement which has both of the components of the bone cement supplied in one flexible package having two separate compartments. When preparing to use the bone cement, a member of the surgical staff removes a temporary seal separating the two compartments and then mixes the two components together by manipulating the flexible package. The flexible package can then be inserted into a bone cement gun having a reusable syringe and a disposable nozzle. Accordingly, the components of the bone cement gun and syringe remain relatively free of bone cement during the bone cement application.

According to still another version of the present invention, the packaging system comprises a vacuum reservoir in communication with the compartment containing the powder component, the powder component being under vacuum.

An advantage of the present invention is to provide a packaging system for bone cement that minimizes the exposure to vapors which are generated during the mixing operation.

Another advantage of the present invention is to provide a packaging system for bone cement that reduces the amount of air mixed into the bone cement that would otherwise occur during traditional cement preparation, thereby reducing the porosity present in the cured bone cement.

Another advantage of the present invention is to provide a packaging system that is adaptable to be placed within a bone cement gun and that minimizes the number of components of the bone cement gun that must be cleaned or replaced due to contact with the bone cement.

An advantage of the present invention is to provide a packaging system wherein a vacuum provides a bone cement with a low porosity, less than about 1 percent.

A further advantage of the present invention is to provide a packaging system for bone cement that is relatively low in cost and relatively easy to use.

BRIEF DESCRIPTION OF THE DRAWINGS

Additional advantages of the present invention will become apparent from the following description and appended claims, taken in conjunction with the accompanying drawings in which:

FIG. 1 is an elevational view of a hip joint prosthesis shown in operative association with a hip and a pelvis;

FIG. 2 is a perspective view of the packaging system for bone cement which is used during the implantation of the hip joint prosthesis shown in FIG. 1 according to the first preferred embodiment of the present invention;

FIGS. 9-11 and FIGS. 10(A) and 10(B) are diagrammatic sectional views showing a further improved packaging system for bone cement having a vacuum reservoir according to preferred embodiments of the present invention;

FIGS. 12(A)-12(E) are diagrammatic sectional views illustrating operational steps of the mixing of the bone cement using the packaging system for bone cement shown in FIG. 9;

FIGS. 14(A)-14(E) are diagrammatic sectional views showing a packaging system for bone cement having a vacuum reservoir according to a further preferred embodiment of the present invention.

DESCRIPTION OF THE PREFERRED EMBODIMENTS

Figure 3:
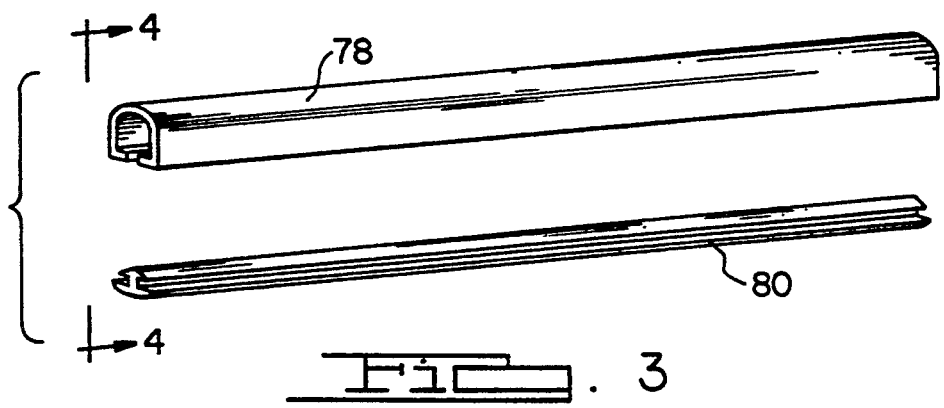
FIG. 3 is a perspective view of the temporary sealing device shown in FIG. 2 according to the first preferred embodiment of the present invention.

The following discussion of the preferred embodiments of the present invention is merely exemplary in nature and is not intended to limit the invention or its application or uses.

Referring now to the drawings in which like reference numerals designate like or corresponding parts throughout the several views, there is shown in FIG. 1 a joint within the human body which is designated generally as reference numeral 10. The joint 10 includes a hip joint prosthesis 12 which is used for transferring a load between the pelvis 14 and a host femur 16. The hip joint prosthesis 12 is used to replace a natural hip after the natural hip has degenerated. While the following discussion will describe the use of the present invention in the context of a hip joint prosthesis, it will be understood that the present invention may also be applicable to other types of prosthetic components including the femoral component for a knee joint prosthesis, the tibial component for a knee joint prosthesis as well as other types of medical implant devices.

The hip joint prosthesis 12 includes a ball head 18 which is sized to fit into a matching acetabular socket 20. The ball head 18 extends from a neck portion 22 which in turn extends from a platform 24 carried by a primary load-bearing member in the form of a stem 26. The stem 26 is operable to be located in a specially reamed cavity 28 in the host femur 16. The stem 26 may be formed of titanium, cobalt chrome, or other suitable materials, and may have various cross-sectional configurations. As will be appreciated by those skilled in the art, the ball head 18 engages the acetabular component 20 which is secured within the pelvis 14.

During the implanting of the hip joint prosthesis 12 into the joint 10 of the patient, the stem 26 and the acetabular component 20 of the hip joint prosthesis 12 are often anchored in place in part by using bone cement. The cementing of these components generally facilitates the attachment of these components to both the host femur 16 and the pelvis 14. The bone cement is normally formed from a methyl methacrylate monomer liquid component and a poly (methyl methacrylate) polymer powder component. To provide x-ray contrast, 5-10% zirconiumoxide or bariumsulphate may also be added to the powder polymer. In addition, a polymerization initiator such as 1-5% benzoylperoxide may be used. The bone cement is applied to the cavity 28 or to the bony acetabulum which are both prepared to anchor the corresponding components of the hip joint prosthesis 12. The application of the bone cement is normally performed by using a bone cement gun as will be more fully described below.

The present invention provides a bone cement packaging system which allows preparation of the bone cement without exposing the bone cement to the environment. This preparation minimizes the amount of air that may become mixed into the bone cement, minimizes objectionable vapors and further allows the preparation of the bone cement in a low cost package which then can be used to deliver the bone cement into the surgical site with the aid of a bone cement gun.

Referring now to FIGS. 2 through 5, a packaging system for bone cement is shown and is designated generally by the reference numeral 50. The packaging system 50 includes a flexible container 52 and a clamp 54. The flexible container 52 comprises a front panel 56 and a rear panel 58, each made of a thin generally impervious flexible film which is more fully described below. In the embodiment shown in FIGS. 2 through 5, the panels 56 and 58 are each formed from a single sheet of flexible film sealed to each other at a bottom edge 60 and side edges 62 and 64. The flexible container 52 further includes a nozzle 66 which is formed as a flat tubular portion and sealed on its edges 68 similar to the edges 60, 62 and 64.

Figure 4:
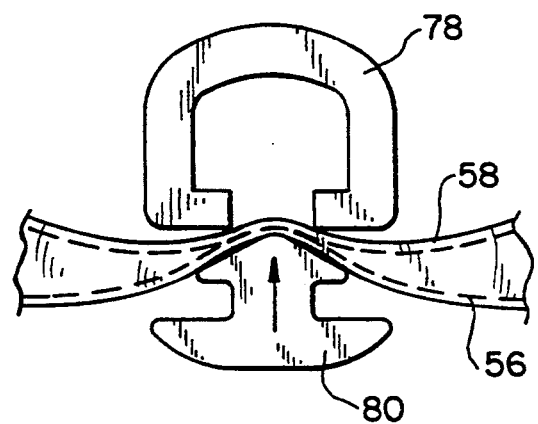
FIG. 4 is a view of the temporary sealing device taken in direction 4—4 in FIG. 3 according to the first preferred embodiment of the present invention.

The clamp 54, best shown in FIGS. 3 and 4, is arranged to provide a temporary seal of the inner surfaces of the panels 56 and 58 to each other along a line extending from an initial point 70 on the sealed edge 62 to a terminal point 72 on the sealed edge 64 to form a first or upper compartment 74 and a second or lower compartment 76. As will be appreciated by those skilled in the art, the clamp 54 is placed on the flexible container 52 prior to being filled with the polymer component and the monomer component of the bone cement. After the lower compartment 76 is filled with the polymer component, the upper compartment 74 may be filled with the monomer component of the bone cement. The method used for filling the flexible container 52 will be more fully described below.

The clamp 54 comprises a C-shaped outer retention member 78 and an I-shaped inner retention member 80 which partially fits within the hollow of the C-shaped outer retention member 78. When the clamp 54 is assembled with respect to the flexible container 52 as shown in FIG. 4, the outer retention member 78 is positioned on the outside of the rear panel 58 and the inner retention member 80 is positioned on the outside of the front panel 56 such that the panels 56 and 58 are pinched together along a pair of parallel lines extending from the initial point 70 to the terminal point 72. The inner retention member 80 has a contoured upper end which fits within the inner hollow of outer retention member 78 and has a thickness substantially equal to the inner distance between the open ends of the C-shaped section of the outside retention member 78 so that a double thickness of panels 56 and 58 is tightly compressed along a pair of parallel lines to form an effective seal. The outer retention member 78 is made of a resilient material so that the inner retention member 80 may be forced into position therein by placing it over the entire length of the opening of the outer retention member 78 and then pressing it into place. Inner retention member 80 has a contoured upper end which can open the open ends of the C-shaped section of the outside retention member 78 to accommodate the inner retention member 80.

Both the outer retention member 78 and the inner retention member 80 are long enough to reach from the initial point 70 to the terminal point 72. Preferably, inner retention member 80 is somewhat longer than outer retention member 78 to provide for a gripping point when the retention members 78 and 80 are to be separated and removed.

The method of packaging the bone cement within the flexible packaging 52 will now be described. The front panel 56 and rear panel 58 are first formed from a thin generally impervious flexible film. The side edges 62 and 64 of the front panel 56 and the rear panel 58 are then secured to each other by heat sealing. The clamp 54 is then placed over the front panel 56 and the rear panel 58 so as to form a temporary seal between the front panel 56 and the rear panel 58 and partially form the upper compartment 74 and the lower compartment 76 under environmentally controlled conditions. The lower compartment 76 is then filled with the powder component of the bone cement via the open end of the nozzle 66. A seal then closes the lower compartment 76. The flexible container 52 is then sterilized employing gamma radiation, electron beam or other means. The monomer component of the bone cement is then filled into the upper compartment 74 under aseptic conditions and then the upper compartment 74 is closed by the seal 60.

Figure 5:
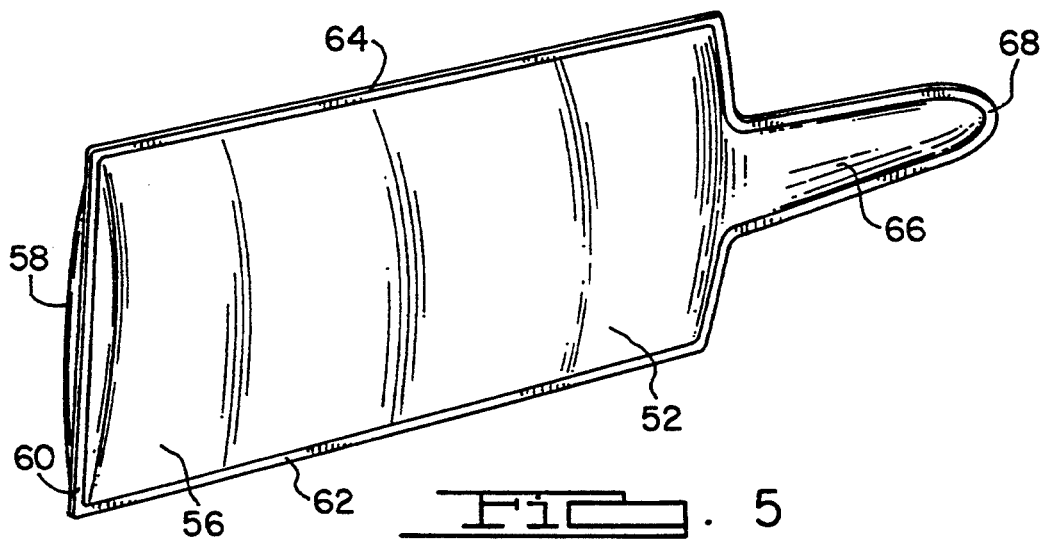
FIG. 5 is a perspective view of the packaging system for bone cement shown in FIG. 2 depicting the packaging system after the temporary sealing device has been removed and the two components of the bone cement are mixed.

When the surgeon decides to use the bone cement within the flexible container 52 and apply the bone cement by hand using the nozzle 66, the inner retention member 80 is separated from the outer retention member 78 to remove the clamp 54 and open the lower compartment 76 to the upper compartment 74 as shown in FIG. 5. The flexible container 52 is then pressed or kneaded so as to mix the individual components of the bone cement. The mixing of the components within the flexible container 52 while the flexible container 52 is intact (i.e., prior to opening) limits the inclusion of air and minimizes the emission of vapors from the components. The flexible container 52 may then be opened by cutting and removing the end of the nozzle 66. Bone cement may then be dispensed by hand by squeezing the flexible container 52.

Figure 6:
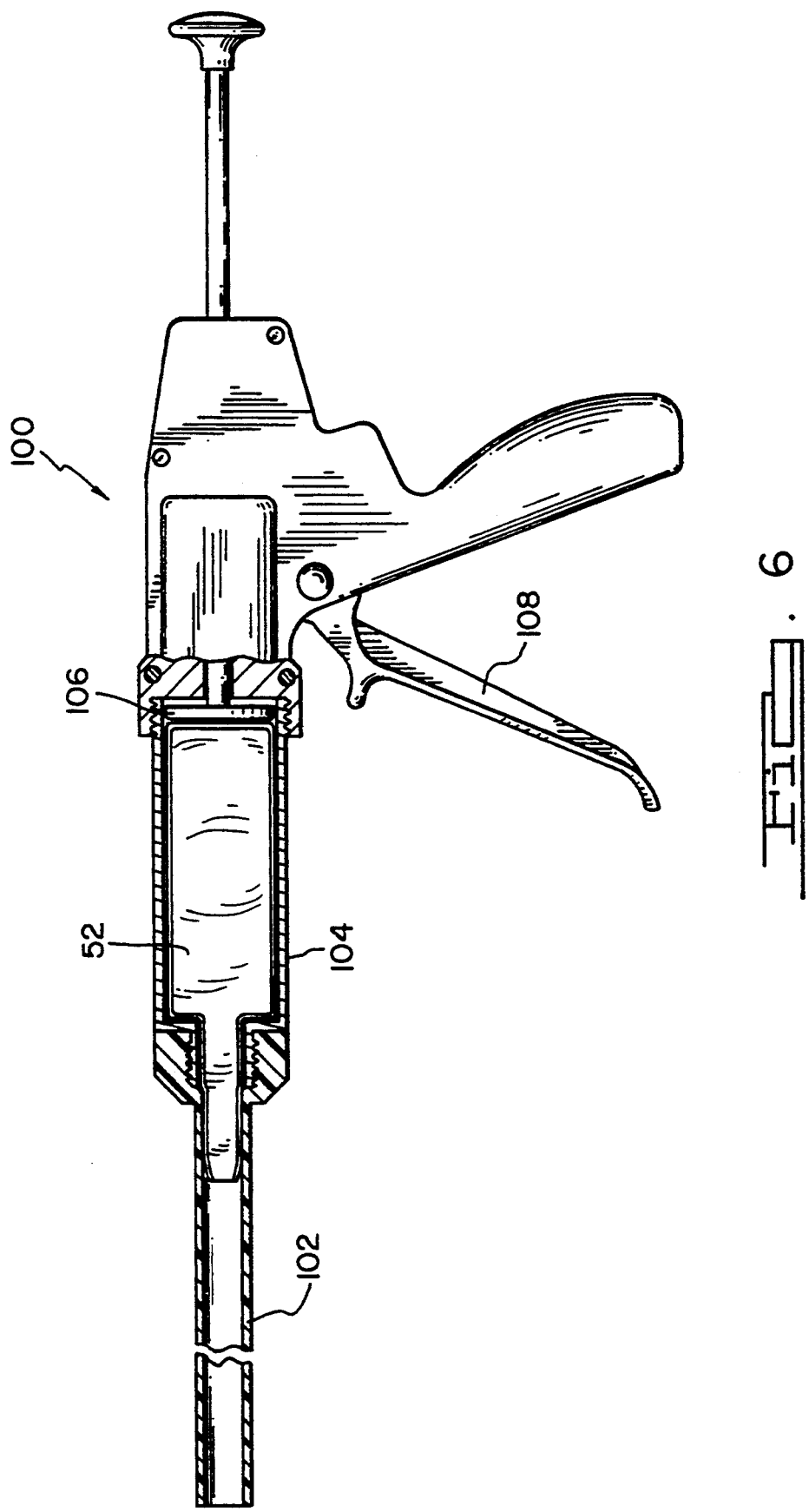
FIG. 6 is a side sectional view of a bone cement gun containing the packaging system for bone cement according to the first preferred embodiment of the present invention.
Figure 7:
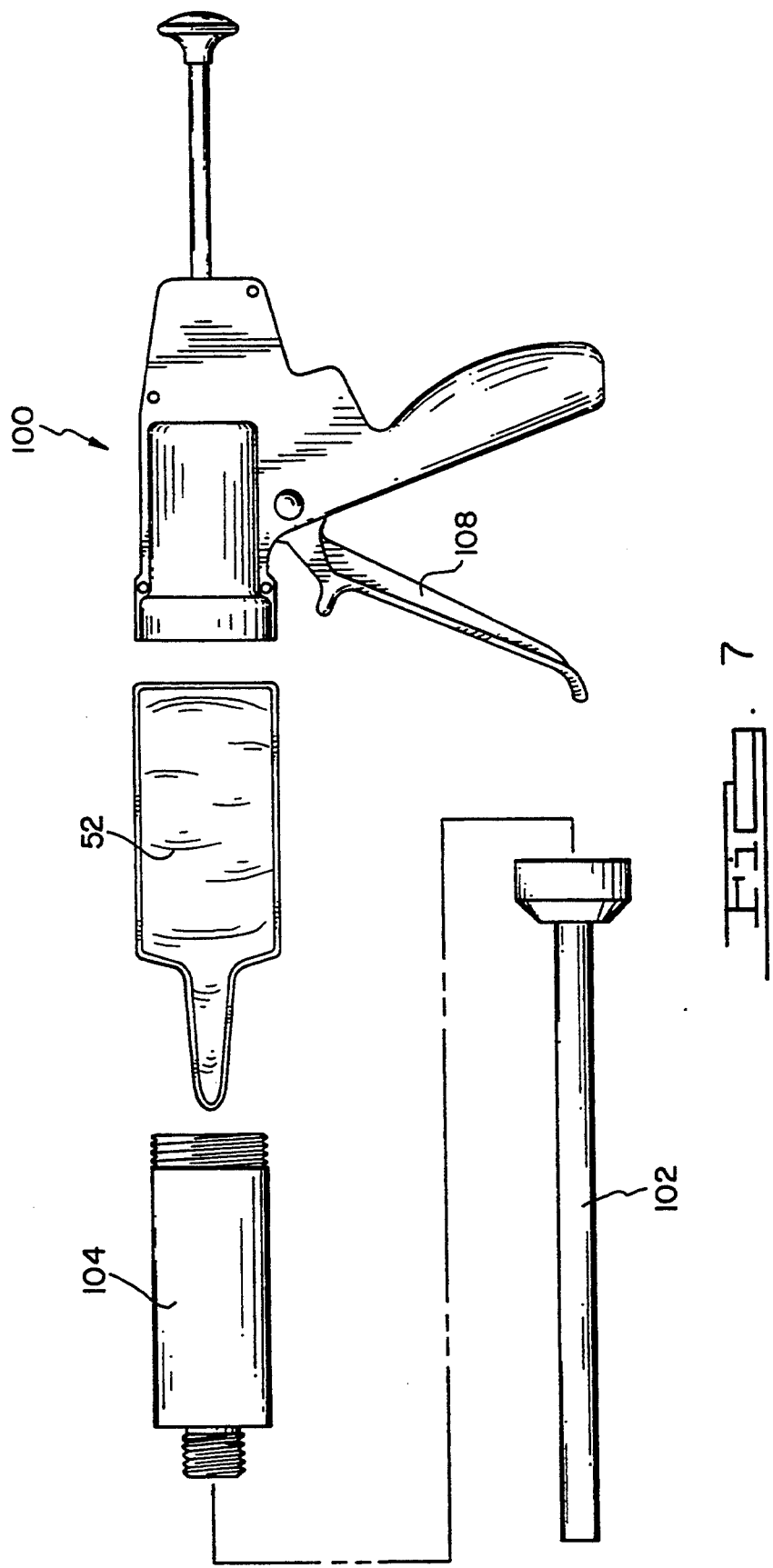
FIG. 7 is an exploded perspective view of the bone cement gun shown in FIG. 6 according to the first preferred embodiment of the present invention.

When the surgeon decides to use the bone cement gun 100 as shown in FIGS. 6 and 7, the above-described procedure is followed and the flexible container 52 is then inserted into a bone cement syringe 104 and the nozzle 66 is opened. After the bone cement syringe 104 is inserted into the bone cement gun 100, a tubular member 102 is then secured to the open end of the bone cement syringe 104 with the nozzle 66 of the flexible container 52 extending into the tubular member 102 as shown in FIG. 6. An actuation mechanism 108 is then squeezed which in turn moves a plunger 106 to the left as shown in FIG. 6 forcing the bone cement out of the flexible container 52 through the tubular member 102. Once the bone cement has been pumped from the bone cement gun 100, the flexible container 52 can be removed from the bone cement syringe 104 leaving a clean bone cement gun 100 and bone cement syringe 104 which then can be reused for dispensing additional quantities of bone cement.

The nature of the thin generally impervious flexible film to be used with the flexible container 52 of the present invention depends upon the nature of the materials to be stored and the conditions under which the materials will be mixed and used. For many materials, polyethylene film is suitable. Other suitable films include teflon, polyester, nylon, ethyl vinyl alcohol, metal foil, laminated glass and various combinations of the foregoing materials. However, it will be appreciated that other suitable materials may also be used. Generally, thermoplastic films are used and the seals 60, 62, 64 and 68 are heat seals. However, thermoplastic films are not essential and the seals 60, 62, 64 and 68 may be adhesive seals.

The nature of the clamp 54 may also vary. The clamp 54 described in connection with the present invention consisting of an I-shaped inner retention member 80 and a C-shaped outer retention member 78, is preferred because of its simplicity and ease of handling. However, other types of clamps suitable for applying pressure to the flexible container 52 may also be used. In addition, it is possible to replace the clamp 54 with an additional separation seal (not shown). In this embodiment, the separation seal can be either a heat seal or an adhesive seal to separate the upper compartment 74 from the lower compartment 76. The strength of this separation seal must be such that it can be broken by placing pressure on either of the compartments 74 and 76 without damaging the panels 56 and 58. This separation seal may also be used in conjunction with the clamp 54.

It will also be appreciated that the flexible container 52 need not be made from separate sheets of film sealed at their bottom edge 60 as shown in FIGS. 2 through 5. The flexible container 52 may be made from a double sized flexible sheet of film folded at the bottom edge 60 thereby providing a folded edge to seal the bottom of flexible container 52. In another embodiment, the flexible container 52 may be made from a segment of a film sleeve, in which case the edges 62 and 64 would be folded edges while bottom edge 60 would be a sealed edge.

Figure 8:
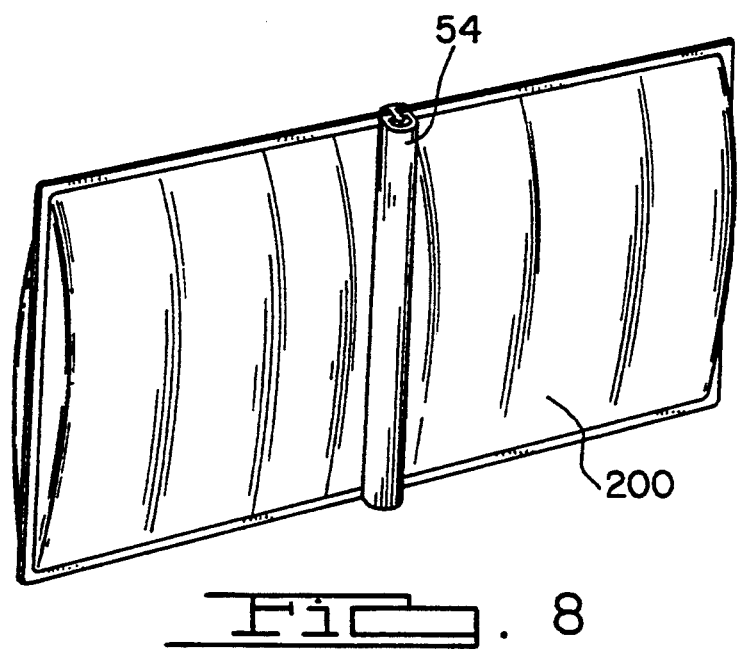
FIG. 8 is a perspective view of the packaging system for bone cement in accordance with another preferred embodiment of the present invention.

While the present invention has been described with respect to a flexible container 52 which is essentially rectangular in shape having a nozzle, it is to be understood that the present invention is applicable to flexible containers of other shapes, such as rectangular, triangular or trapezoidal and may have curved edges. For example, FIG. 8 shows a perspective view of a packaging system 50 having a rectangular shape which does not have the nozzle 66. In this embodiment, after removal of the clamp 54 and the mixing of the two components of bone cement, the end of the flexible container can be removed and the bone cement can be dispensed from the flexible container 52 by hand or by a roller (not shown). The surgeon can then place the bone cement within the appropriate bone cavity by using any type of an applicator.

In addition, the location of the clamp 54 need not be along a midline as shown in the figures, but may be closer to the bottom edge or the top edge to provide compartments of different sizes if the nature of the final composition of the bone cement requires different amounts of each component be used. In addition, the clamp 54 may be disposed lengthwise on the flexible container 52 rather than longitudinally. Furthermore, various other types of tubular members may be attached to the bone cement syringe to accommodate the needs of the surgeon. Finally, the components of the bone cement may be vacuum packaged within the flexible container.

In accordance with another improved version, the present invention provides a flexible packaging system for in situ admixing of two reactive components to produce bone cement, the packaging system comprising a first compartment containing a predetermined quantity of a liquid component, a second compartment containing a predetermined quantity of a powder component, and a seal for temporarily isolating the liquid component from the powder component. The second compartment is maintained under vacuum and either encloses a vacuum reservoir, or is in communication with a vacuum reservoir that is an integral part of the packaging system. The vacuum reservoir has a sufficiently large volume to take up the residual gases which will be replaced in the interstitial voids between the particles of the powder component by the liquid component upon release or breaking of the seal between the first and second compartments.

The force which transfers the liquid component into the second compartment to combine with the powder component is thus the pressure differential between the atmospheric pressure acting on the walls of the first compartment and the pressure prevailing in the second compartment. The function of the vacuum reservoir is to maintain a sufficiently low pressure in the second compartment until the powder component has been completely flooded by the liquid component. Following the admixing, the flexible container holding the bone cement is placed inside a rigid cylinder open at one end to receive the flexible container and provided with an opening at its other end to which a suitable nozzle can be connected.

In another version of the present invention, the second compartment has a nozzle-like extension formed as an integral part of the flexible wall, and this nozzle is passed through the opening in the cylinder and cut open to permit passage of bone cement after mixing. The cylinder is then placed in a bone cement gun having a plunger or piston fitting into the open end of the cylinder. By activating the lever, the piston moves into the cylinder and compresses the flexible container forcing the bone cement out through the nozzle.

FIGS. 9-14 illustrate these various preferred embodiments of the present invention. In each, the lower compartment 76 containing the powder component is temporarily isolated from the liquid component by divider means and either encloses a vacuum reservoir or is in communication with a vacuum reservoir that is an integral part of the flexible container 52. As mentioned before the vacuum reservoir has a volume sufficiently large to hold under reduced pressure the residual air which will be displaced from the interstitial voids between the particles of the powder component by the liquid component upon removal of the clamp 54. By using a vacuum reservoir, the liquid component will voluntarily flow to fill the vacuum created in the voids between the particles of the powder component. The mixing of the bone cement is therefore "static" in the sense that the kneading of the flexible container 52 may not be necessary and the porosity is even lower compared to the porosity of the cement provided from the container according to the invention without the vacuum reservoir.

FIG. 9 shows one alternative embodiment having such a vacuum reservoir. The packaging system 50 shown in FIG. 9 comprises the flexible container 52 made by heat sealing front panel 56 and the rear panel 58 along the edges 60–64 and 68. The packaging system 50 is divided into the first or upper compartment 74 and the second or lower compartment 76 by the elongated clamp 54. The clamp 54 is operable to squeeze the medial portions of the front and rear panels 56 and 58 together so as to interlock with the panels 56 and 58, thereby forming a tight seal so as to isolate the powder component 82 from the liquid component 84.

It is possible that the flexible container 52 may be divided into the upper and lower compartments 74 and 76 by a weld line (not shown) which leaves only a small opening of 5-20 mm unwelded. The clamp 54 is then used to seal the small opening so as to form a complete seal between the upper and lower compartments 74 and 76. The use of the weld line and the reduced opening, in combination with the clamp 54, reduces the possibility that the liquid component will diffuse into the powder component over a long period of time. When the clamp 54 is removed, it is observed that the flow of the liquid component can be initiated by a slight pressure on the upper compartment 74 and the liquid component will then rapidly spread out through the entire lower compartment 76. The unwelded opening may be placed in the middle or to one side near the edge of the flexible container 52 with equally good results.

The clamp 54 associated with the packaging system 50 of the embodiment of the present invention shown in FIG. 9 is similar to that shown with respect to the embodiment shown in FIG. 2. In this regard, the clamp 54 and the interlocked relation between the panels 56 and 58 of the flexible container 52 and the clamp 54 is shown in FIGS. 10(A)–10(C). The clamp 54 comprises the rigid C-shaped outer retention member 78 and the I-shaped inner retention member 80. When the clamp 54 is in place, the two panels of film 56 and 58 tightly engage each other and interlock by the clamp 54 so as to form a substantially airtight seal between the compartments 74 and 76 and isolate the powder component 82 from the liquid component 84.

Disposed within the lower compartment 76 is a vacuum reservoir 86. In the embodiment shown, the vacuum reservoir 86 comprises a cylindrical polyethylene tube 88 closed at its opposite end by the filters 90 and 92 although it is to be understood that only one end need be closed by a filter. The filters 90 and 92 allow passage of air through the tube interior 94 of the cylindrical polyethylene tube 88, but prevent the particles of the powder component from entering the interior 94 of the vacuum reservoir 86. The filters 90 and 92 may consist of plugs of cotton, wool, nitrocellulose wool, or air permeable Tyvec film welded onto the ends of the tube. The wool will act as a plug which will swell when the monomer contacts it whereby to seal off the product chamber.

It should be understood that the vacuum reservoir 86 can comprise a separate vacuum cylinder, having a frangible opening, which permits the user to break the cylinder opening just prior to use. When such an approach is used, the flexible container 52 does not have to be placed under vacuum when the flexible container 52 is initially filled with the liquid and the powder components. For example, the clamp 54 would isolate the liquid and powder components in the compartments 74 and 76, and the vacuum reservoir 86 would be heat sealed into position in the nozzle 66 without a vacuum being drawn in the lower compartment 76. When the user is ready to prepare the bone cement, the frangible seal of the vacuum reservoir 86 would be broken, such as by a twisting motion, thereby reducing the pressure in the lower compartment 76. The vacuum reservoir 86 would be configured to have a volume sufficiently large to hold under reduced pressure the air from the lower compartment 76 as well as the residual air that will be displaced from the powder component by the liquid component upon removal of the clamp 54.

The method of operation using the packaging system 50 according to this embodiment of the present invention is shown in FIGS. 12(A) through 12(E). In FIG. 12(A), the flexible container 52 is shown filled with the powder component 82 while the upper compartment 74 is ready to be filled with the liquid component 84. The powder component 82 is initially placed within the lower compartment 76 through the nozzle 66 and a vacuum reservoir 86 is placed inside the nozzle 66. Thereafter a vacuum is drawn on the nozzle 66 such that the interior of the nozzle 66 and the lower compartment 76 are maintained in a substantially airless state. The nozzle 66 is then heat sealed at the edge 68 while the vacuum is maintained inside the lower compartment 76 and the nozzle 66. The liquid component 84 is then placed in the upper compartment 74 in a manner similar to that described above and then upper compartment 74 is sealed. Care is taken so that little, if any, air enters the upper compartment 74 while the upper compartment 74 is being filled with the liquid component. The resulting structure of the packaging system 50 is that which is shown in FIG. 9.

FIG. 12(B) shows the flexible container 52 shortly after the clamp 54 has been removed and the liquid component 84 has started to wet the powder component 82 so as to form bone cement represented by the area 96. The liquid component 84 is driven towards and into the powder component 82 by the atmospheric pressure acting on the upper compartment 74 containing the liquid component 84. The residual air in the interstitial voids between the particles of the powder component 82 is drawn into the vacuum reservoir 86. In FIG. 12(C), the in situ wetting of the liquid component 84 into the powder component 82 is complete. All the voids between the particles of the powder component 82 are filled by the liquid component 84, and the residual air is held inside the vacuum reservoir 86 at a partial vacuum. Accordingly, little if any manipulation of the flexible container 52 is required to mix the bone cement. The bone cement within the flexible container 52 may then be dispensed in the manner shown in FIGS. 12(D) and 12(E). The flexible container 52 is placed within a bone cement syringe 104 with the nozzle 66 passing through the nipple 110 of the bone cement syringe 104. The nozzle 66, including the vacuum reservoir 86, is then removed. The bone cement syringe 104 is then placed within the bone cement gun 100 and the tubular member 102 is attached to the bone cement syringe 104. The plunger 106 of the bone cement gun 100 is then displaced toward the flexible container 52 by manipulation of the activation member 108 of the bone cement gun 100. As the plunger 106 compresses the flexible container 52, bone cement is delivered through the tubular member 102. By choice of suitable material, the flexible container 52 can be fully compressed leaving only a small fraction of bone cement inside the flexible container 52.

Figure 13:
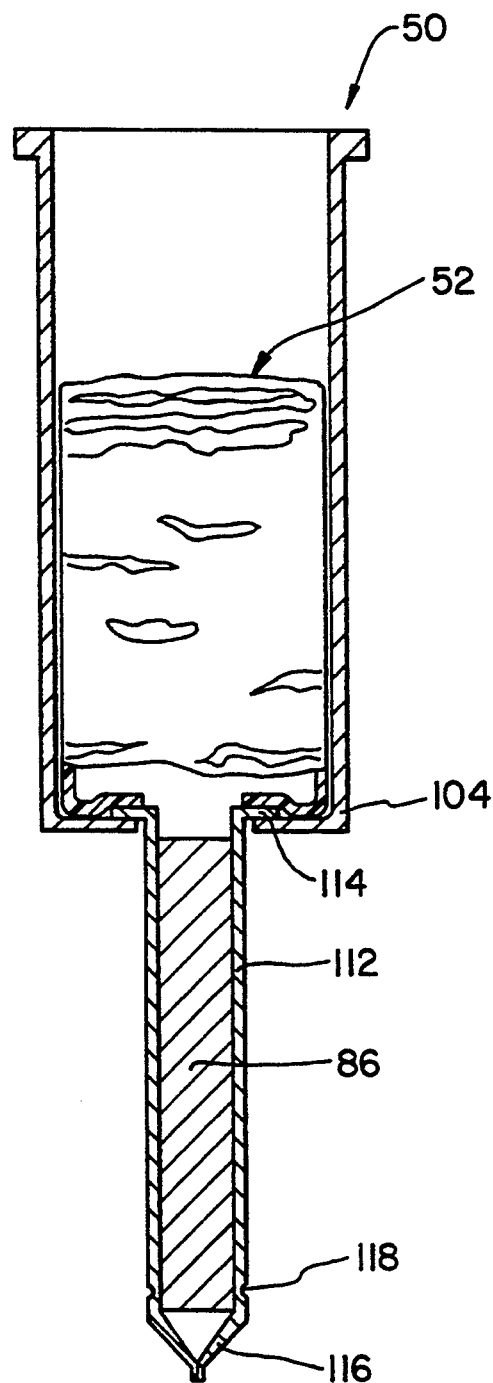
FIG. 13 is a section view showing a packaging system for bone cement having a vacuum reservoir according to another preferred embodiment of the present invention.

Another preferred embodiment of the present invention is shown in FIG. 13. According to this embodiment, the flexible container 52 includes a vacuum reservoir 86 which has a slender cylinder of open cell foam. The material used for the foam of the vacuum reservoir 86 may be any cellular material having a significant number of pores or interconnected cells. The size of the pores is preferably, at least in the end facing the powder component, of such size that particles of the powder component do not enter the vacuum reservoir 86. Also the foam must be rigid enough to maintain its shape during the flooding of the liquid component into the powder component. Examples of suitable materials from which the foam can be made are open-cell polyethylene foam and cotton fibers formed into a slender cylindrical plug with highest density at the innermost end.

The flexible container 52 according to this embodiment further includes a cylindrical nozzle 112. The cylindrical nozzle 112 has one end sealed to the flexible container 52 around a flange 114 and its other end provided with a tip 116 which is heat sealed. During formation of the packaging system 50 according to this embodiment of the present invention, the lower compartment 76 is filled with the powder component, and then the vacuum reservoir 86 is inserted into the nozzle 112. The air within the voids between the particles of the powder component is then evacuated through the foam in the vacuum reservoir 86, and then the tip 116 is sealed. The vacuum which is within the vacuum reservoir 86 provides the necessary driving force to accomplish the desired mixing of the liquid component with the powder component.

Mixing of the liquid and powder components occurs upon removal of the clamp 54. When this mixing is complete the flexible container 52 is placed inside the bone cement syringe 104 with the nozzle 112 extending through a suitable hole of the bone cement syringe 104. The tip 116 of the flexible container 52 is cut along a groove 118 and then the vacuum reservoir 86 is removed. When the bone cement syringe 104 has been placed in the bone cement gun 100 and a suitable tubular member 102 has been attached, bone cement may then be dispensed from the flexible container 52.

Another preferred embodiment according to the present invention is shown in FIGS. 14(A)–14(E). In this regard, the compartments which are used for storing the liquid and powder components are interconnected by a narrow passage that is initially sealed but is broken when the components of the bone cement are to be mixed. The use of a narrow passage to allow the liquid component to flow into the powder component simplifies the sealing of the upper and lower compartments and reduces a possible long term leakage between the compartments.

According to this embodiment, a flexible container 52 is provided with upper and lower compartments 74 and 76 for the liquid and powder components, a vacuum reservoir 86 is disposed substantially entirely inside the lower compartment 76 and surrounded by the powder component, and an isolating seal 120 in the form of a strip of foil is welded to the flexible package 52 in a narrow passage 122 extending between the upper and lower compartments 74 and 76. As shown in FIG. 14(A), the vacuum reservoir 86 comprises an elongated hollow cylindrical tube 124 which has a conical pointed end 126 located in the passage 122 adjacent to the isolating seal 120 and an open end plugged with a filter element 128 which will retain particles but allows air to pass.

In use, the cylindrical tube 124 is driven through to the narrow passage 122 and towards the upper compartment 74 until the conical pointed end 126 of the vacuum reservoir 86 pierces the isolating seal 120 (see FIG. 14(B)), allowing the liquid component to enter the lower compartment 76 having the powder component (see FIG. 14(C)). After mixing (see FIG. 14(D)), the vacuum reservoir 86 may be further urged through the narrow passage 122 and entirely into the now empty upper compartment 74. The flexible container 52 may then be severed at the narrow passage 122, and the upper compartment 74 and vacuum reservoir 86 removed, thereby leaving an opening 130 through which the bone cement can be expelled (see FIG. 14(E)).

In the following Examples, various comparative tests are reported which further describe the present invention.

EXAMPLE 1

A commercial bone cement, sold under the trademark "SURGICAL SIMPLEX P", was packed in a flexible container of the type disclosed in FIG. 9, omitting the vacuum reservoir and without vacuum over the powder. One compartment of the flexible container was filled with 40 g powder, comprising poly-methylmethacrylate and a copolymer of methyl methacrylate and styrene, together with benzoylperoxide and bariumsulphate. The other compartment was filled with 20 ml monomer comprising methylmethacrylate containing an amine accelerator.

The bone cement was prepared by removing the clamp and blending the powder component into the liquid component by kneading the flexible container taking care to obtain a homogeneous mixture. Following kneading, the flexible container was placed into a bone cement syringe and the bone cement was delivered using a bone cement gun through a 200 mm long tubular nozzle. Following cure at 37° C. for 24 hours, the average porosity of the cement was measured and was found to be 8.24% with a standard deviation of 0.66%. This illustrates the considerable level of air in the bone cement.

EXAMPLE 2

In a similar experiment, a commercial bone cement, CMW-1 was used. The average porosity was determined to be 9.16% with a standard deviation of 1.68%.

EXAMPLE 3

"BONELOC" bone cement was packed in flexible containers of the type disclosed in FIG. 9, omitting the vacuum reservoir, but with a full vacuum put on the powder component for 20 seconds and heat sealing while under vacuum.

Upon removal of the clamp, the liquid component was observed to flow into the static bed of the powder component. The flow was rapid at first, but slowed down and stopped before full wetting was obtained. In some instances, attempts were made to obtain full mixing by kneading of the flexible container. In one test, the unwetted powder component was removed and the remaining cement mixture was used. The ratio between the powder component and the liquid component was kept constant in all tests, but the total weight of ingredients varied from test to test as shown in Table 1 set forth below. All test samples were prepared for testing of porosity. The following observations were made:

Example 3(A):

The liquid component flow stopped before full mixing. About ½ to 1 cm of the unwetted powder component remained at the short end of the flexible container. The spout was cut open, and the dry powder component was removed. Using a cement gun, the remaining mixture was expelled without any mechanical mixing.

The initial flow of liquid component was rapid, but gradually stopped, leaving a band of dry powder component along the short end of the flexible container. The cement was mixed by kneading the flexible container until all of the powder component was wetted.

Example 3(C):

The same observations were made as in Example 3(B). About 80% of the powder component was wetted initially, and the flexible container was kneaded to obtain full mixing.

Example 3(D):

In this Example, about 1.5 cm of the unwetted powder component remained after the liquid component flow had stopped. Attempts were made to get the remaining unwetted powder component wetted by gently stroking the wet cement from one end of the flexible container to the other. About 0.7 g of the dry powder component was removed before the cement was expelled.

TABLE 1

| Test Identity | Amounts Used | | | |
| --- | --- | --- | --- | --- |
| | Powder (gm) | Liquid (gm) | Air (%) | Average Porosity (%) |
| Example 3 (A) | 45.6 | 20.4 | 0.0 | 0.60 |
| | | | 0.49 | |
| | | | 1.12 | |
| | | | 0.84 | |
| Example 3 (B) | 39.1 | 17.5 | 2.33 | 2.78 |
| | | | 3.72 | |
| | | | 2.29 | |
| Example 3 (C) | 60.7 | 27.2 | 1.69 | 3.02 |
| | | | 3.54 | |
| | | | 3.82 | |
| Example 3 (D) | 53.7 | 24.1 | 2.09 | 3.02 |
| | | | 3.62 | |
| | | | 3.36 | |

As shown in Table 1, by applying vacuum over the powder component, the liquid component can be made to flow into the internal void of the powder component and mix with about 80% of the powder component. The remaining powder component is unwetted unless some form of kneading or mechanical mixing is used. Examples 3(B), 3(C) and 3(D) show the more preferable level of porosity obtained by having a vacuum in the powder compartment of the flexible bag. Example 3(A) shows the still more preferable level of porosity which can be obtained by the static mixing without kneading the dry powder containing residual air into the cement.

EXAMPLE 4

Three flexible containers with bone cement similar to the ones used in Example 3 were prepared. One flexible container had a vacuum reservoir made from a 5 cm length of 10 mm diameter polyethylene tube placed in the long spout on top of the powder component. The other two flexible containers were made without vacuum reservoir. The evacuation time used was 60 seconds. Further details of the tests are set forth below in Table 2.

TABLE 2

| Test Identity | Powder (gm) | Liquid (gm) | Vacuum Reservoir | Air (%) | Comments |
|---|---|---|---|---|---|
| Example 4 (A) | 60.6 | 27.7 | — | 0.68 | 8 mm band of unwetted powder |
| Example 4 (B) | 61.0 | 27.4 | 5 cm long, 10 mm diameter | 0.86 | All powder wetted after 30 seconds; no additional manipulation |
| Example 4 (C) | 54.4 | 24.4 | | 2.47 | 1 cm band of un-wetted powder; attempted mixing by gentle strokes; 3 g unwetted powder removed at start of cement delivery. |

As shown in Table 2, without a vacuum reservoir some of the powder component remained unmixed, but the fraction of cement which was mixed had very low porosity. If a vacuum reservoir was added to the flexible container, it became possible to have full mixing of the components and the very low porosity of Example 4(B).

EXAMPLE 5

The bone cement and the flexible containers of the experiments of Example 3 were made with various sizes of vacuum reservoirs. The vacuum reservoirs were made from plastic tube of 10 mm. internal diameter.

In Example 5(A), the vacuum reservoir had a length of 2.5 cm. When the clamp was removed the liquid component flowed down through the entire powder component bed in about 55 seconds. When the flexible container was opened, there was no dry powder component remaining. A small amount of residual liquid component was found adjacent to the liquid component compartment of the flexible container. The cement was less viscous in this end and more viscous towards the vacuum reservoir.

In Example 5(B), using a 5 cm vacuum reservoir, the wetting was completed in about 40 seconds. There was no dry powder component or free liquid component to observe and the gradient in viscosity was much reduced.

In Example 5(C), the vacuum reservoir was 10 cm long. The liquid component flow was very rapid and complete mixing was obtained in less than 20 seconds. There was no difference in viscosity observed between the two ends of the cement, and there was no residual free liquid component adjacent to the compartment where the liquid component was stored. When the spout was opened and the vacuum reservoir was removed, one or two drops of free liquid component which had been drawn through the powder was found on top of the cement.

From the above discussion, it will be appreciated that the process of mixing the bone cement is "static" mixing. In this regard, the flooding of the powder component by the liquid component occurs by the pressure differential created by the atmospheric pressure acting on the flexible container 52 and the vacuum in the free space associated with the voids between the particles of the powder component. As the liquid component fills the voids of the powder component, the pressure in the free space increases according to an equation which, without the vacuum reservoir 86, is $P_t \times V_t = C$, where $P_t$ is pressure at time t, $V_t$ is the corresponding volume of the free space (hereinafter "free volume") and C is a constant. At time zero (i.e., before mixing is initiated), the equation reads $P_o \times V_o = C$. Thus the driving force $\Delta p$ is:

$$\Delta p = P_a - P_o(V_o/V_t)$$

$P_a$ being the ambient pressure.

The smaller the free volume $V_t$ becomes, the more rapid the pressure increases until the pressure in the free space is slightly less than the pressure acting upon the liquid component, and the flow of the liquid component terminates. By providing the vacuum reservoir 86 of volume $V_r$, a situation is created where the free volume, which becomes $V_t + V_r$, will be large enough to maintain flow until $V_t$ has become zero. This occurs when all voids inside the powder component have been filled by the liquid component and no unmixed powder remains in the flexible container 52.

The minimal volume of the vacuum reservoir 86 will depend on the free volume $V_o$ inside the powder component, the flow resistance for the liquid component through the powder component and the amount of residual air within the flexible container 52. If the resistance to flow of the liquid component is small, the driving force $\Delta p$ can be small, and a relatively small vacuum reservoir 86 will be able to maintain the driving force above the minimum $\Delta P_{minimum}$ required to provide the flow of the liquid component required to fill all voids inside the powder component. Also, the smaller the amount of residual air within the flexible container 52, the smaller the vacuum reservoir 86 may be. This correlation can be expressed by the following equation:

$$\Delta p = P_a - \frac{P_o(V_o + V_r)}{V_r} \geqq \Delta P_{min}$$

or $$V_r \geqq \frac{P_o V_o}{P_a - \Delta P_{min} - P_o}$$

As an illustration of these interrelationships, the experiments of Example 5 may be used. The amount of the powder component was 62.5 g having a free volume $V_o$ of 30.6 ml. With this particular powder, a driving force $\Delta p$ of about 0.3 bar was required in order to maintain a flow of liquid component until the end of the mixing process. The volume $V_r$ of the vacuum reservoir was 1.6 ml.

In Example 5(A), the initial pressure $P_o$ was 0.01 bar and free volume was 30.6 ml and the volume of the vacuum reservoir was 1.6 ml. The minimum volume of the vacuum reservoir 86 calculated using the equation above is 0.44 ml and with a practical volume of 1.6 ml the packaging system 50 will function. Had the initial pressure $P_o$ been 0.1 bar, the minimum size of the vacuum reservoir 86 would have been 5.1 ml. Accordingly, the small vacuum reservoir used in Example 5(A) would have resulted in an incomplete mixing. The larger vacuum reservoir used in Example 5(C), however, has a volume of 6.4 ml and would give a full wetting at an initial pressure $P_o$ of 0.1 bar.

The driving force $\Delta p$ depends on the geometry of the interconnected voids in the powder component and the viscosity of the liquid component. The more open the structure of the powder component, and the lower the viscosity of the liquid component, the smaller will be the driving force required to mix the components, and therefore the volume of the vacuum reservoir 86 may approach $V_r$ as determined by the above equation. In some powder components, the internal structure has such small dimensions that the flow of the liquid component, especially when much of the liquid component has been delivered to the powder component, becomes relatively slow. In such cases, it may be desirable to use a vacuum reservoir 86 which is several times larger (e.g., 2 to 10 times larger) than the minimum volume $V_r$ calculated above.

In a similar fashion, a larger vacuum reservoir 86 should also be used when available mixing time is limited by some physical or chemical process which is initiated by the liquid component and powder component coming into contact. If for example the liquid component dissolves the powder component, the viscosity of the liquid component may increase and the internal structure of the voids in the powder component will break down. If these processes are rapid, the flow of the liquid component may be effectively stopped due to increased flow resistance before complete mixing has been achieved. In such cases, a larger vacuum reservoir 86 should be used combined with a low initial pressure $P_o$ to give a rapid flow of the liquid component through the powder component.

A larger vacuum reservoir 86 should also be used when a rapid polymerization reaction is initiated, and it is desired to have a homogeneous reaction throughout the mixture. In such cases, the volume of the vacuum reservoir 86 may be equal to or larger (e.g., 2 to 4 times) the free volume $V_o$ of the powder component. Where limitations are less strict, the volume of the vacuum reservoir 86 may be as low as 0.05 $V_o$ but preferably not below 0.1 $V_o$. Where diffusion of air through the walls of the flexible container 52 during storage may be taken into account, the volume of the vacuum reservoir 86 is most preferably not below 0.2 $V_o$.

The initial pressure $P_o$ at the start of mixing should be as low as possible to provide the smallest amount of residual air within the flexible container 52 while maintaining the necessary driving force for mixing to occur. In commercial vacuum packing machines, the vacuum may be as high as 99.5% or 0.005 bar absolute. In practice, diffusion of air through the walls of the flexible container 52 will reduce this vacuum during storage. Also, gas may be produced from the powder component, for instance, during sterilization by beta or gamma rays. The initial pressure $P_o$ should therefore be below 0.25 bar, preferably below 0.12 bar, and most preferably below 0.08 bar.

There appears to be no well defined upper limit to the size of the vacuum reservoir 86 other than practical considerations such as the size of the flexible container 52. A larger vacuum reservoir 86 will increase the speed by which the powder component is mixed with the liquid component. A larger vacuum reservoir 86 will also give a more homogenous mixture in systems where the powder component dissolves or swells in the liquid component such as in bone cement. A larger vacuum reservoir will also compensate for partial loss of vacuum due to diffusion of atmospheric gases into the flexible container 52 during storage. In such circumstances, the vacuum reservoir 86 may be considerably larger (such as 1.5 to 2 times larger than the free space inside the powder component). This allows a design where the vacuum reservoir 86 is sealed from the lower compartment 76 and, if desired, the vacuum in the lower compartment 76 may then be partly or wholly eliminated. This is because the vacuum needed to mix the liquid component with the powder component is introduced immediately prior to mixing by breaking the seal between the vacuum reservoir 86 and the lower compartment 76. Separating the vacuum reservoir 86 from the lower compartment 76 in this manner may be useful to reduce the pressure difference across the temporary seal between the powder component and the liquid component during storage or to permit the use of certain preferred flexible materials for the lower compartment 76 which have insufficient barrier properties for long term storage. As will be appreciated by those skilled in the art, the material from which the vacuum reservoir is made should have higher barrier properties when the material forming the lower compartment 76 does not.

Generally, any compartment within the flexible container 52 having walls rigid enough to withstand the outside pressure and maintain a vacuum over time may function as a vacuum reservoir. As discussed above, the vacuum reservoir 86 may be made as an integral part of the flexible container 52 by placing a rigid hollow body, such as the cylindrical polyethylene tube 88 shown in FIG. 11, inside the flexible container 52. It will be understood that the rigid hollow body prevents the walls of the flexible container 52 from collapsing so that a vacuum may be formed in the lower compartment 76. The rigid hollow body may have other geometries so long as at least a portion of the body is hollow. In addition, the walls of the flexible container 52 may also be supported by porous rigid bodies such as open-cell rigid foams of polymers or metals. Furthermore, the rigid hollow body may also be made from other cylindrical members such as aluminum tubing.

It will also be appreciated that the vacuum reservoir 86 may be collapsible. As an example, a vacuum reservoir 86 may be a flat bag filled with a high density rigid open-cell foam of size $50 \times 50 \times 20$ millimeters. When the flexible container 50 is evacuated, the vacuum reservoir 86 will be compressed into a thin wafer with a thickness of 2 millimeters and the volume of the vacuum reservoir 86 will be 3.75 ml. It will be appreciated that the compressed foam exerts a pressure on the flexible walls, attempting to separate the walls and expand the volume of the vacuum reservoir 86. During mixing, residual air will move into the vacuum reservoir 86 and as the vacuum is decreased by the residual air, the vacuum reservoir 86 expands and maintains an underpressure inside the powder component. It will be understood that in this type of vacuum reservoir, the "vacuum capacity" is stored as compressive strain in the flexible foam. This type of vacuum reservoir can thus give large capacity at limited space. The flexible foams commercially available have a limited load carrying capacity so the vacuum which can be maintained by the compressed foam is limited to about 5–20%. Accordingly, vacuum reservoirs of this type using flexible foams are best used with porous solids where the liquid component will flow under a driving force Δp of 0.05 to 0.2 bar.

It will be understood that the size of the vacuum reservoir 86 can be calculated using the formulas and directions given above. In cases where one or more parameters required in the calculation is not known, simple experimentation with vacuum reservoirs of different sizes will provide the information required to complete the calculation.

It will also be understood that in the formulas above, the driving force Δp will be larger at the beginning of mixing when the vacuum is highest and will decrease as the free volume is reduced. $\Delta P_{min}$ is the pressure difference below which the flow becomes too slow, and Δp is thus correlated to the acceptable mixing time. In practice, the choice of the volume of the vacuum reservoir 86 will often be based on observation of the time it takes for the liquid component to flow through the entire bed of the powder component. For some applications, the acceptable time may be as high as 2 to 4 minutes, while for applications involving a catalyzed reaction, the maximum time will be from about 1 to about 2 minutes. For demanding applications involving both a rapid polymerization reaction as well as a dissolution of the porous structure such as in bone cements, the mixing time should be in the range of from about 5 to about 60 seconds, preferably from about 5 to about 30 seconds.

The two component bone cements used with the packaging system 50 of the present invention can be any two or more component system which comprises at least one powder component having an internal free void which will allow passage and uptake of a corresponding liquid component. Examples of such systems are bone and dental cements as well as other compositions where the liquid component comprises methacrylate monomers together with the usual polymerization initiators, amine accelerators and radiopaquifiers and colorants. The powder component may be a homopolymer or a copolymer of methyl methacrylate with other methacrylates or vinyl monomers such as styrene. The liquid component will preferably be a mixture of monomers. The weight ratio of powder component to liquid component is preferably below about 3.0 and more preferably between about 1.8 and about 2.5.

The shape and size of the particles of the powder component is preferably such that a system of interconnecting voids will be present which will not collapse under the pressure exerted on the powder component while under vacuum, or become clogged by too rapid dissolution in the liquid component when wetting has begun. It has been observed that certain powder components used in commercial bone cements comprise a large proportion of finely milled polymethacrylate powder which may in certain instances block the passage of the liquid component after only a fraction of the powder component has been wetted.

Accordingly, in a preferred version, the powder component used in practicing the invention comprises a majority of spherical particles having a size larger than 10 μm preferably above 25 μm. Preferably the powder component is a mixture of particles covering a range of sizes up to 100 μm. A preferred powder component has an evacuated interspace comprising more than 30%, and more preferably, more than 35% of the bulk volume of the vacuum packed powder. In a particularly preferred version, at least the major part of the very fine radiopaque particles, which may be zirconium oxide particles less than about 2 μm, have been coated onto the surface of the polymer particles.

While the above detailed description describes the preferred embodiments of the present invention, it should be understood that the present invention is susceptible to modification, variation and alteration without deviating from the scope and fair meaning of the subjoined claims. Thus, for example, it will be understood that the apparatus of the invention may be useful in the preparation of compositions other than the bone cement described.

What is claimed is:

1. A flexible container for packaging liquid and powder components that are to be mixed within the container to form bone cement, said container comprising:
   dividing means for dividing the container into first and second compartments and for isolating the components from one another, said first compartment containing said liquid component and said second compartment containing said powder component under vacuum, and
   a vacuum reservoir means in communication with said second compartment, said vacuum means being of sufficient size to ensure take up of substantially all residual interstitial gasses and thereby ensure thorough admixing of the liquid and powder components upon release of the dividing means.

2. The container according to claim 1 comprising an elongated pocket portion extending from and in communication with said second compartment wherein said vacuum reservoir means is disposed in said pocket portion.

3. The container according to claim 2, wherein said vacuum reservoir comprises an elongated hollow cylinder having an interior and closed at least at one end by a respective filter element, the interior of said cylinder being of sufficient volume to receive and hold under reduced pressure the interstitial air.

4. The container according to claim 2, wherein said vacuum reservoir comprises an elongated cylinder formed of an open-cell foam, said open-cell foam being of sufficient free volume to receive and hold under reduced pressure the interstitial air.

5. The container according to claim 1, wherein said dividing means comprises a heat seal between said first and second compartments, said heat seal including an opening for passing said liquid component into the second compartment and a clamp in removably interlocked relation with said heat seal to removably close said opening.

6. The container according to claim 1, wherein the weight ratio of the powder component to the liquid component is below about 3.

7. The container according to claim 1, wherein the weight ratio of said powder component to said liquid component is between about 1.8 and about 2.5.

8. The container according to claim 1, wherein the volume of said vacuum reservoir is greater than about 0.05 times the free volume in the powder.

9. The container according to claim 8, wherein the volume of said vacuum reservoir is about 2 to about 4 times the free volume in the powder.

10. The container according to claim 1, wherein the majority of said powder component is comprised of spherical particles having a diameter larger than about 25 μm.

* * * * *